United States Patent
Kosecoff

(10) Patent No.: US 12,178,895 B2
(45) Date of Patent: Dec. 31, 2024

(54) HAIR CONTOURING TREATMENTS USING PHOTORESPONSIVE HYDROGELS

(71) Applicant: L'OREAL, Paris (FR)

(72) Inventor: David B. Kosecoff, San Francisco, CA (US)

(73) Assignee: L'Oreal, Paris (FR)

(*) Notice: Subject to any disclaimer, the term of this patent is extended or adjusted under 35 U.S.C. 154(b) by 333 days.

(21) Appl. No.: 17/490,878

(22) Filed: Sep. 30, 2021

(65) Prior Publication Data
US 2023/0101494 A1   Mar. 30, 2023

(51) Int. Cl.
| | |
|---|---|
| A45D 37/00 | (2006.01) |
| A61K 8/04 | (2006.01) |
| A61K 8/19 | (2006.01) |
| A61K 8/81 | (2006.01) |
| A61Q 5/04 | (2006.01) |

(Continued)

(52) U.S. Cl.
CPC ............... *A61K 8/042* (2013.01); *A61K 8/19* (2013.01); *A61K 8/8158* (2013.01); *A61K 8/8194* (2013.01); *A61Q 5/04* (2013.01); *A45D 2/00* (2013.01); *A45D 2200/205* (2013.01); *A61K 2800/413* (2013.01); *A61K 2800/81* (2013.01); *A61K 2800/95* (2013.01); *H05B 47/105* (2020.01)

(58) Field of Classification Search
CPC ...... A45D 2/00; A45D 1/00; A45D 2200/205; H05B 47/105; A61K 8/042; A61K 8/8194; A61K 2800/413; A61K 2800/81; A61K 2800/95

See application file for complete search history.

(56) References Cited

U.S. PATENT DOCUMENTS

2021/0042807 A1*   2/2021   Charraud ........... G06Q 30/0641

FOREIGN PATENT DOCUMENTS

| DE | 10 2012 210 272 A1 | 12/2013 |
| WO | 2007/096344 A1 | 8/2007 |
| WO | 2018/237346 A1 | 12/2018 |

OTHER PUBLICATIONS

DE 102012210272 A1 computer translation EPO (Year: 2012).*

(Continued)

*Primary Examiner* — Rachel R Steitz
(74) *Attorney, Agent, or Firm* — Christensen O'Connor Johnson Kindness PLLC

(57) ABSTRACT

Devices, systems, materials, and methods for contouring a volume of hair are described. A hair contouring device can include a contouring source. The contouring source can be configured to generate contouring electromagnetic radiation within a first energy range to induce a conformation change of a hydrogel formulation. The hair contouring device can include a fixing source. The fixing source can be configured to generate curing electromagnetic radiation within a second energy range to induce a photo-curing transition of the hydrogel formulation. The hair contouring device can include an input component. The hair contouring device can also include control circuitry, electrically coupled with the contouring source, the fixing source, and the input component. The control circuitry can be configured to receive an input from the input component and to control the contouring source or the fixing source in accordance with the input.

19 Claims, 6 Drawing Sheets

(51) Int. Cl.
 *A45D 2/00* (2006.01)
 *H05B 47/105* (2020.01)

(56) References Cited

OTHER PUBLICATIONS

France Search Report and Written Opinion mailed Jul. 4, 2022, issued in Application No. FR2113455, filed Dec. 14, 2021, 6 pages.
Seog-Jin Jeon et al.; "Shape-Morphing Materials from Stimuli-Responsive Hydrogel Hybrids"; Accounts of Chemical Research; Feb. 9, 2017; pp. 161-169; vol. 50, Issue No. 2; American Chemical Society.
Kyunki Kim et al.; "Light-driven shape morphing, assembly, and motion of nanocomposite gel surfers"; Advanced Materials; May 12, 2019; pp. 1-19; vol. 31, No. 27; WILEY-VCH Verlag Gmbh & Co. KGaA.
Lei Li et al.; "Design and Applications of Photoresponsive Hydrogels"; Advanced Materials; 2019; pp. 1-17; vol. 31; WILEY-VCH Verlag Gmbh & Co. KGaA.
International Search Report and Written Opinion as mailed on Jan. 18, 2023, issued in corresponding International Application No. PCT/US2022/077285, filed Sep. 29, 2022, 8 pages.
International Preliminary Report on Patentability for International Application No. PCT/US2022/077285, mailed Apr. 11, 2024.

\* cited by examiner

HAIR CONTOURING TREATMENTS USING PHOTORESPONSIVE HYDROGELS

SUMMARY

Devices, systems, materials, and methods for contouring a volume of hair are described. A hair contouring device can include a contouring source. The contouring source can be configured to generate contouring electromagnetic radiation within a first energy range to induce a conformation change of a hydrogel formulation. The hair contouring device can include a fixing source. The fixing source can be configured to generate curing electromagnetic radiation within a second energy range to induce a photo-curing transition of the hydrogel formulation. The hair contouring device can include an input component. The hair contouring device can also include control circuitry, electrically coupled with the contouring source, the fixing source, and the input component. The control circuitry can be configured to receive an input from the input component and to control the contouring source or the fixing source in accordance with the input.

In some embodiments, the conformation change of the hydrogel formulation includes a volumetric expansion or contraction of the hydrogel formulation. The photo-curing transition of the hydrogel formulation can include a cross-linking of the hydrogel formulation. The input can include a contouring control or a fixing control. The control circuitry can be configured to activate the contouring source in response to receiving the contouring control. The control circuitry can be configured to activate the curing source in response to receiving the fixing control.

In some embodiments, the hair contouring device further includes a radiation sensor, electronically coupled with the control circuitry and one or more non-transitory memory devices, electronically coupled with the control circuitry. The one or more non-transitory memory devices can store computer-readable instructions that, when executed by one or more processors of the control circuitry, cause the control circuitry to perform operations. The operations can include generating a mapping of a biological surface using the radiation sensor, the biological surface comprising hair and the hydrogel formulation, the mapping describing a volume of the hair relative to the biological surface. The operations can include generating a projection of a hair contouring design onto the mapping, wherein the hair contouring design defines a contouring treatment to be applied to the volume of the hair. The operations can include determining an exposure profile and an exposure duration using the projection. The operations can include exposing the volume of the hair to the contouring electromagnetic radiation using the contouring source in accordance with the exposure profile and the exposure duration. The operations can also include exposing the volume of the hair to the curing electromagnetic radiation using the fixing source.

In some embodiments, the instructions, when executed by the one or more processors, further cause the control circuitry to perform operations including receiving the hair contouring design via the input component, wherein the input component comprises communication circuitry configured to pair with a client computing device and to receive the input from the client computing device. The hydrogel formulation can include photo-responsive filaments, and wherein the photo-responsive filaments exhibit anisotropic deformation in response to exposure to the contouring electromagnetic radiation. The first energy range can correspond to near-ultraviolet wavelengths from about 300 nm to about 400 nm. The first energy range can correspond to near-infrared wavelengths from about 750 nm to about 1400 nm. The hydrogel formulation can include upconverting nanoparticles, wherein the upconverting nanoparticles emit ultraviolet photons when exposed to the contouring electromagnetic radiation. The first energy range can correspond to visible wavelengths from about 400 nm to about 750 nm. The hydrogel formulation can include a photo-initiator dispersed in poly(ethylene glycol) diacrylate. The hydrogel formulation can include an absorber material dispersed in a hydrogel comprising poly(N-isopropylacrylamide) (pNIPAm) copolymerized with spiropyrane. The absorber material can include chromium oxide or iron oxide particles. The second energy range can correspond to near-ultraviolet wavelengths, visible wavelengths, or near-infrared wavelengths, being non-overlapping with the first energy range.

A method of contouring hair using a hydrogel formulation can include applying the hydrogel formulation to a volume of hair. The method can include exposing the volume of hair to contouring electromagnetic radiation within a first energy range to induce a conformation change of the hydrogel formulation, the conformation change including a volumetric expansion or contraction of the hydrogel formulation. The method can also include exposing the volume of hair to curing electromagnetic radiation within a second energy range to induce a photo-curing transition of the hydrogel formulation, the photo-curing transition including a cross-linking of the hydrogel formulation. The contouring electromagnetic radiation and the curing electromagnetic radiation can be generated by a hair contouring device including a contouring source of the contouring electromagnetic radiation, a fixing source of the curing electromagnetic radiation, an input component, and control circuitry, the control circuitry being electrically coupled with the contouring source, the fixing source, and the input component.

In some embodiments, the method includes generating a mapping of the volume of hair using a radiation sensor, the radiation sensor being electronically coupled with the control circuitry. The method includes generating a projection of a hair contouring design onto the mapping, wherein the hair contouring design defines a contouring treatment to be applied to the volume of hair. The method also includes determining an exposure profile and an exposure duration using the projection. Exposing the volume of hair to the contouring electromagnetic radiation can include controlling the contouring source in accordance with the exposure profile and the exposure duration. The method can include receiving the hair contouring design via communication circuitry configured to pair with a client computing device and to receive the input from the client computing device. The method can include receiving an input from the input component, the input comprising a contouring control or a fixing control. The method can include activating the contouring source in response to receiving the contouring control. The method can also include activating the fixing source in response to receiving the fixing control. The hydrogel formulation can include photo-responsive filaments. The photo-responsive filaments can exhibit anisotropic deformation in response to exposure to the contouring electromagnetic radiation.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Figure 1:
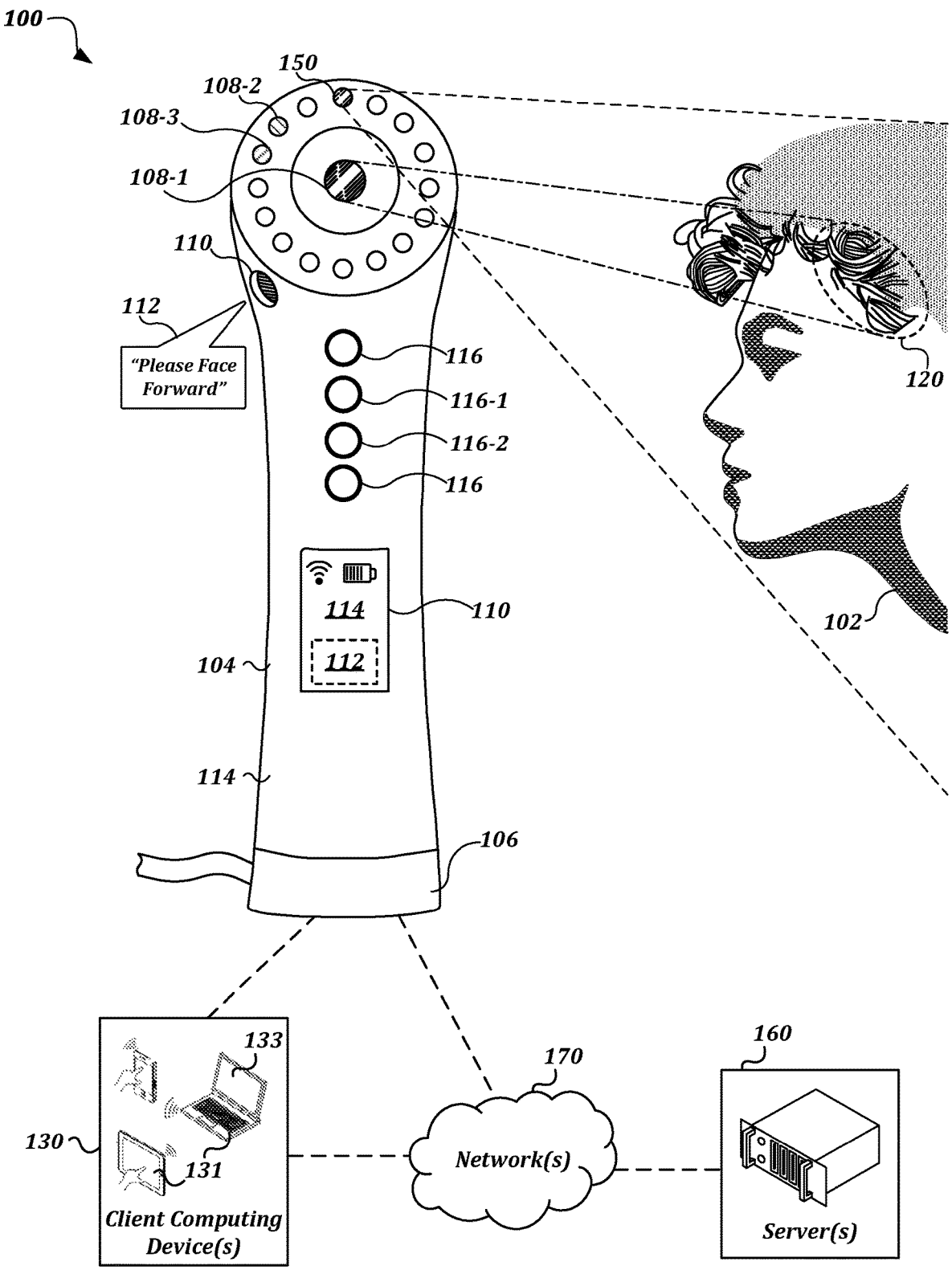
FIG. 1 is a schematic diagram illustrating an embodiment of a system for contouring a volume of hair, in accordance with various embodiments.

In the above-referenced drawings, like reference numerals refer to like parts throughout the various views unless otherwise specified. Not all instances of an element are necessarily labeled to simplify the drawings where appropriate. The drawings are not necessarily to scale, emphasis instead being placed upon illustrating the principles being described. The foregoing aspects and many of the attendant advantages of this invention will become more readily appreciated as the same become better understood by reference to the following detailed description, when taken in conjunction with the accompanying drawings.

DETAILED DESCRIPTION

Contouring hair in patterns and according to designs can be difficult by hand. For curling, shaping, straightening, or relaxing hair, chemicals and heat are routinely used that can damage hair and harm health over time. Burns of the scalp and hands are common, and relaxer chemicals can vaporize and be inhaled, which can cause health impacts after regular and/or frequent exposure. Where and how to apply heat and chemicals in an effective, aesthetically desirable way is a challenging, artistic act. In certain instances, cosmetic contouring of hair includes both curling a portion of the hair, straightening a different portion of the hair, and layering the two as part of an overall contouring treatment. In some cases, hair contouring designs involve repeated applications of heat and chemicals in a professional context, requiring specialized training, equipment, and supplies.

Systems, methods, and photo-responsive materials are described for applying contouring treatments to a volume of hair using one or more electromagnetic radiation sources. Described embodiments use photo-responsive materials exhibiting shape-change, contraction, or expansion to apply one or more contouring treatments mapped to the hair and/or a body surface using a projection of a contouring treatment design onto a 3D mapping of the body surface. Described embodiments are useful in many contexts, including professional styling and home styling. In the context of such applications, described embodiments provide precision and greater ease of use over complex manual routines and improve accessibility of at-home contouring treatment without a salon visit.

In described embodiments, a biocompatible hydrogel formulation can be applied to the hair. The material can have properties such that when cured will physically contract and/or expand, creating a net curling, straining, shaping, or relaxing effect on the hair. In this way, the hair can be temporarily contoured without the use of heat, chemicals, or salon equipment and expertise. The hydrogel formulation can be photopolymerized or otherwise modified using exposure to one or more radiation sources to a desired shape across various depths on and through the volume of hair and can be actuated/modulated/addressed by one or more wavelengths, as part of applying the contouring treatment to the hair.

Without being limited to a specific system or method, systems and methods for applying such contouring treatments are also described in the context of a sensor-bearing system. Sensors suitable for use in described embodiments include 2-dimensional (2D) or 3-dimensional (3D) cameras, proximity sensors, or other integrated or peripheral cameras or sensors. Depth sensors are used in some embodiments to obtain 3D information about surfaces and include a range of possible hardware suitable for this purpose, including RGB or infrared stereoscopic cameras, laser or infrared LiDAR sensors, and dot projectors. 3D scans enable improved measurement of hair and body surfaces and allow depth sensing, which can help to determine, for example, how far the hair and/or the body surface is from the camera, or detailed information about the hair. Reference points obtained through high-quality 3D scanning in accordance with described embodiments provides greater accuracy for determining location than traditional reference points obtained with 2D imaging, such as eyes, lips, noses, or other prominent facial features, and are particularly helpful for tracking hair relative to more prominent and/or more easily tracked features.

In some embodiments, systems for applying a contouring treatment to a volume of hair include an electromagnetic radiation source, physically coupled to a portable or handheld device, the radiation source configured to emit one or more discrete electromagnetic stimuli of a character and for a duration sufficient to induce a localized change in a photo-responsive material disposed on a surface of a biological subject, wherein each discrete electromagnetic stimulus has a discrete peak emission wavelength. In this context, the term "discrete electromagnetic stimuli" is used in reference to energy emitted from a source, including, but not limited to, photons, radio waves, microwaves, x-rays, or ions. In the forthcoming paragraphs, description of discrete electromagnetic stimuli focuses on photons in the ultraviolet, near ultraviolet, visible, near infrared, and infrared ranges, produced by one or more radiation sources. In this context, the term "peak emission wavelength" is used in reference to an energy (e.g., as described in terms of wavelength, wavenumber, electron-volts, etc.) at which a local and/or global maximum in emission intensity is observed, which can be described by an emission intensity distribution as a function of energy. In the forthcoming paragraphs, peak emission wavelength refers to an example of a central wavelength, describing a radiation source from which the output emission distribution is centered or otherwise distributed around the peak emission wavelength.

In some embodiments, systems are described in terms of a means for determining an irradiation profile for each of the one or more treatment regions to contour each respective treatment region as part of applying the contouring treatment. In this context, the term "means" is used in reference to the systems described in the forthcoming paragraphs, such as the computational circuitry described above as well as systems and components for defining surface mappings of biological subjects. The system can also include means for creating structures on a surface of a biological subject by inducing a localized change in a photo-responsive material. In this context the means can be understood to describe sources and control systems for generating discrete electromagnetic stimuli, such as radiation sources, directed toward a biological subject.

The systems can include a camera including radiation sensors to receive photons having energies in the visible, ultraviolet, infrared or other spectra. The systems can also include a controller operably coupled to the radiation source and the camera and including computational circuitry configured to initiate irradiation of the photo-responsive material disposed on the volume of hair in accordance with a respective irradiation profile to induce a localized change in shape or state of the photo-responsive material. In this context, the term "computational circuitry" is used in reference to operational components of a computer system, including but not limited to volatile and/or nonvolatile memory devices, data transmission subsystems (e.g., bus), and/or software and/or firmware provided to implement contouring treatments using photo-responsive materials. In this context, the term "controller" is used in reference to operational electronic components configured to control active components of systems described herein, in accordance with electronic instructions from the computer system (e.g., processor(s) and computational circuitry).

The systems described expose the hair with one or more actuating wavelengths in accordance with the contouring treatment as mapped onto the 3D information collected by the sensors. In this way, the photo-responsive material, applied to a volume of hair, can be made to apply one or more contouring morphology changes as described by the contouring treatment design accurately and precisely by illumination with the actuating wavelengths rather than manual application of heat or force to the hair. Advantageously, the materials, systems, and methods described also provide improved accessibility to users with limited mobility or dexterity, for whom contouring treatments, such as precise shaping of hair, can otherwise involve assistance by another person.

FIG. 1 is a schematic illustration of an example system 100 incorporating sensors and one or more radiation sources for application of contouring treatments, according to various embodiments. While the embodiments of the photo-responsive material described in reference to the forthcoming figures are illustrated in the context of example system 100, alternative approaches are also contemplated. The system 100 is not intended as the sole system for use with the photo-responsive materials described below.

As part of the example system 100, one or more cameras 150 of a hair contouring device 104 capture images of a subject's face 102. In the example shown, the hair contouring device 104 is a purpose-built mobile computing device including one or more radiation sources 108, and one or more user interface elements 110 to prompt the subject with visual and/or auditory prompts 112. For example, the interface elements 110 can be or include a display 114 electronically coupled with the computer system to generate a visual prompt. Additionally or alternatively, the hair contouring device 104 can include an acoustic speaker to generate an auditory prompt (e.g., "please face forward").

The camera(s) 150 can be or include one or more radiation sensors configured to detect photons in one or more energy ranges corresponding to ultraviolet, near ultraviolet, visible, near infrared, and/or infrared. The radiation source(s) 108 can be configured such that the hair contouring device 104 can emit one or more discrete wavelength channels. In this way the system 100 can appear aesthetically as an ordinary cosmetic or bathroom mirror without outward indication that the system 100 incorporates electronics, cameras 150, or radiation sources 108. For example, the components of the hair contouring device 104 can be integrated into a housing 114 that appears similar to a consumer cosmetic device, such as a light-therapy device, rather than an electronics system. In this example, the housing 114 can conceal power sources, heat management systems, and other components. In some embodiments, the hair contouring device 104 can removeably couple with a base 106. The base 106 can include electrical components to connect the hair contouring device 104 to electrical power, for example, for charging internal batteries. In this way, the hair contouring device 104 can function as a portable and/or handheld device that can use steered beams of actuating radiation or can be used to manually guide actuating radiation to volumes of hair to be contoured.

While the hair contouring device 104 is illustrated in a particular configuration (e.g., as a device having multiple radiation sources and sensors clustered at one end), additional and/or alternative form factors are contemplated. For example, the system 100 can include a smartphone or tablet computer in communication with the hair contouring device 104, such that one or more computer-executable operations are undertaken by the smartphone or tablet computer rather than by the hair contouring device 104. In this way, the hair contouring device 104 can be or include smaller housings 114, including, but not limited to, a cosmetics compact or an electronic peripheral configured to electronically couple with a smartphone or tablet computer that includes the camera 150, the radiation source(s) 108, or both. Similarly, the hair contouring device 104 can be integrated into a full-size wall mirror, such that the camera(s) 150 and the radiation source(s) 108 can be positioned behind the mirror. In such a configuration, the system 100 can be installed as a fixture, rather than as a portable system and the mirror can be configured to conceal the camera(s) 150, and the radiation source(s) 108.

The radiation source 108 can include one or more optics configured to form a beam and to scan the beam. The optics can include lenses or mirrors internal to the housing 114 that can be actuated or otherwise controlled to direct a beam from the radiation source(s) 108 to a volume of hair 120. For example, the radiation source(s) 108 can be or include one or more laser sources or other monochromatic sources. In some embodiments, the radiation source(s) 108 includes multiple light-emitting diodes corresponding to the plurality of discrete wavelength channels. Similarly, the radiation source(s) 108 can be or include a continuous source (e.g., a tungsten halide or broad-spectrum source) and a plurality of bandpass filters to generate the discrete wavelength channels used by the system 100 to apply a contouring treatment. Addressable arrays of illumination data, described in more detail in reference to FIG. 2A and FIG. 2B, can be implemented by DLP techniques.

Radiation source(s) 108 can include multiple types of sources capable of generating contouring and/or curing radiation of different energies. For example, hair contouring device 104 can include one or more contouring sources 108-1 and one or more curing sources 108-3. In the illustrated embodiment of the hair contouring device 104, the contouring source(s) 108-1 are illustrated as being disposed in a central region, and being surrounded by multiple curing sources 108-3 disposed about the periphery of the contouring source(s) 108-1 in an arrangement similar to conventional light-therapy devices. It is understood, however, the number and arrangement of contouring source(s) 108-1 and curing source(s) 108-3 can differ. For example, the radiation sources 108 can be integrated into a single source incorporating multiple miniature emitters, such a micro-LEDs, and can be multiplexed using gratings such that a single optical aperture is the point of exit of both types of electromagnetic radiation. Alternatively, the different radiation sources 108 can be separated into different regions of the hair contouring device 104. Advantageously, such configurations each provide different functional advantages, beyond representing a simple aesthetic choice. For example, spatially isolating the different radiation sources 108 can reduce the likelihood that a user will confuse the different sources 108 during manual operation. Combining the sources 108 into a single source, by contrast, can improve targeting of the radiation exposure onto specific regions of the volume of hair 120, for example, through beam steering components or through providing more precise manual control afforded by a narrower exposure area.

In some embodiments, radiation sources 108 include one or more second contouring sources 108-2, configured to emit contouring radiation at a different energy than the contouring source(s) 108-1. The second contouring source(s) 108-2 can be used to reverse the effect of the contouring source(s) 108-1, where the photo-induced shape change of the hydrogel formulation is reversible under exposure to a different energy range of electromagnetic radiation, as described in more detail in reference to FIG. 4. In an illustrative example, the contouring source(s) 108-1 can emit visible wavelength photons, while the second contouring source(s) 108-2 can emit near-ultraviolet wavelength photons.

In some embodiments, multiple contouring sources 108-1 are disposed on a surface of the hair contouring device 104, rather than a single contouring source 108-1 as is shown in FIG. 1. To that end, the hair contouring device 104 can be controlled through input components 116 in a manner similar to a hand-held light source, such as an electric flashlight or torch. The hair contouring device 104 can include multiple input components 116, of which a first input component 116-1 can generate a contouring control and a second input component 116-2 can generate a fixing control, respectively configured to activate the contouring source(s) 108-1 and the curing sources 108-3. In this way, operating the hair contouring device 104 can include a user providing an input using the input component(s) 116 to generate the contouring control to shape the volume of hair 120, and to generate the fixing control to fix the volume of hair 120.

In some embodiments, the input components 116 include one or more "soft" input components in a user interface, presented via the user interface 110 and/or the client computing device(s) 130. For example, the input components 116 can include a menu, a browser environment, or an application environment that is in electronic communication with the client computing device(s) 130 and/or server(s) 160, such that the hair contouring device 104 can receive a hair contouring design via the input component(s) 116.

The hair contouring device 104 can be in electronic communication with additional systems via a network or over near-field communication protocols (e.g., wifi, bluetooth, etc.). For example, the hair contouring device 104 can pair with one or more client computing devices 130, such as a smart phone or tablet, from which the hair contouring device 104 can receive an identifier of a contouring treatment design. Similarly, the hair contouring device 104 can communicate with one or more servers 160, storing numerical representations of designs, and can access the designs from the server(s) 160. The server(s) 160 can be a remote server or can be a local server, where the terms "remote" and "local" are used both to refer to physical proximity to the system 100 and to denote whether the hair contouring device 104 and the server are configured to communicate over a network 170, such as the internet, or a distributed network system (e.g., a cloud system). In some cases, the hair contouring device 104 can store design data locally for a number of contouring treatments, for example, using a non-transitory computer readable storage medium (e.g., SSD flash memory, hard disk drives, etc.). For example, the hair contouring device 104 can receive newly released contouring treatment design data and associated metadata from the server(s) 160, such as identifier information and interface data (e.g., images representing the contouring treatment on a model), which can be provided via the interface elements 110 or via the mobile electronic device. In such cases, the system can be configured to operate with intermittent or no network connectivity.

In some embodiments, the camera 150 acts as a far-field camera positioned and configured to capture video or still images of subject's face 102, as well as the volume of hair 120, such that the volume of hair 120 is within the field of view 152 of the camera(s) 150. In the example shown, the volume of hair 120 is shown as a portion near the left cheek of the subject's face 102, but the volume of hair 120 can cover a larger portion of the subject's hair, such as the entirety of the subject's hair. In some embodiments, the camera unit 150 includes more than one camera, such as for stereoscopic image or video capture and/or depth sensing. In some embodiments, the camera unit 150 also includes one or more sensors other than cameras (e.g., a LiDAR sensor or infrared dot projector for depth sensing, a proximity sensor for proximity detection, etc.). In some embodiments, an infrared dot projector or other structured light detector projects patterned radiation onto a surface, and reflections from the surface are measured by an infrared camera as part of mapping the surface of hair and face. When working in conjunction with a 3D camera, these depth measurements can be mapped onto a captured 3D image. This approach is used in some embodiments to generate a 3D model of the volume of hair 120, and for real-time tracking of additional features to be used for mapping a contouring treatment onto the volume of hair 120.

Figure 2A:
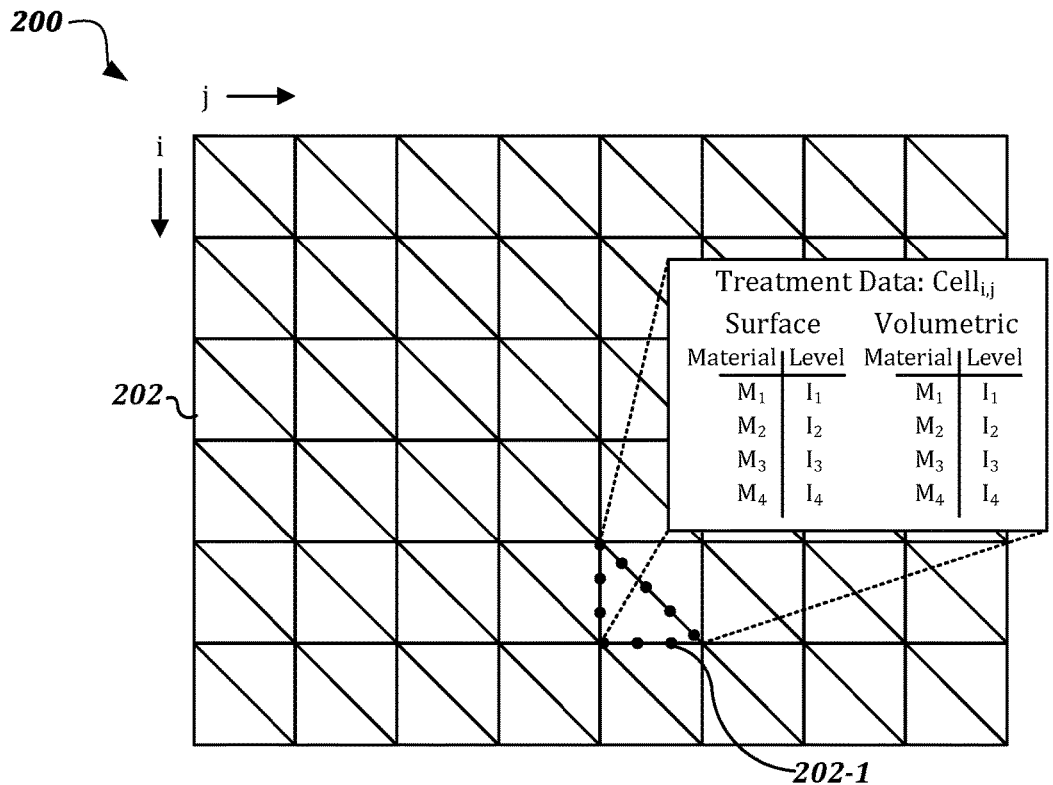
FIG. 2A is a schematic illustration of a numerical representation of a contouring treatment as a polygonal mesh including a tensor of treatment data in a face-on direction and a low-angle direction, in accordance with various embodiments.

FIG. 2A is a schematic illustration of a numerical representation of a contouring treatment 200 as a polygonal mesh including a tensor of treatment data for contouring treatments, in accordance with various embodiments. The treatment design 200 represents an exemplary visualization of a contouring treatment design, including multiple polygons 202, where each polygon 202 represents a unit of the numerical representation, akin to a pixel in a digital image. Where the system implementing the processes described herein (e.g., system 100 of FIG. 1) can project the design 200 onto a surface mapping of a user's face (e.g., subject's face 102 of FIG. 1), the polygons 202 can be or include triangles or other shapes that provide greater flexibility for projection and surface mapping relative to square or rectangular pixels.

As shown, a first polygon 202-1 of the design 200, referenced as $Cell_{i,j}$ in the i-j plane of the numerical representation, can include multiple types of treatment data corresponding to different layers of the contouring treatment design 200. For example, the design data for the first polygon 202-1 can include, but is not limited to, a surface treatment tuple and a volumetric treatment tuple, indicating two different treatments to be generated by the system 100 at different positions within the volume of hair 120. Each tuple can include treatment level information corresponding to the photo-responsive materials incorporated into a photo-responsive formulation. For example, the photo-responsive formulation can include one, two, three, four, five, or more different photo-responsive materials. In some embodiments, one or more of the materials can expand under illumination at a characteristic wavelength, while others can contract, harden, or change color in response to illumination at a respective characteristic wavelength. Further, the photo-responsive materials can be actuated by ultraviolet, visible, or infrared light, such that surface treatments can be effected by a first wavelength that is absorbed by the volume of hair 120, while a volumetric treatment can be effected by a second wavelength that is transmitted into the volume of hair 120.

By selectively modulating the photo-responsive materials in accordance with the treatment levels for each polygon, the treatment design 200 can be applied the volume of hair 120. As described in more detail in reference to FIG. 3-FIG. 4, treatments can be designed to provide contouring on the surface and/or as a volumetric contouring treatment of the volume of hair 120. While each polygon 202 is illustrated as having a uniform characteristic size, it is to be understood that the polygons are representative of a tensor of contouring information that is referenced by cell entries in i-j space, rather than in cartesian coordinates. In this way, the first polygon 202-1 can be larger or smaller than neighboring polygons 202 when projected into a physical dimension, such as when applied to a facial mapping of a user for application of the design 200 (e.g., volume of hair 120 of FIG. 1).

Figure 2B:
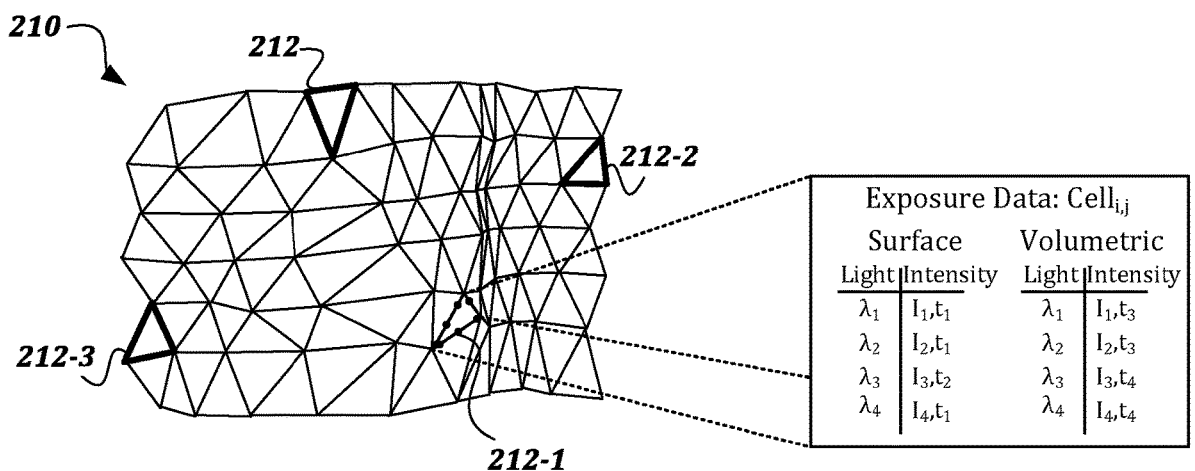
FIG. 2B is a schematic illustration of a 3-dimensional model projection of the contouring treatment onto a face mapping, in accordance with various embodiments.

FIG. 2B is a schematic illustration of an example 3-dimensional projection 210 of the treatment design 200 onto a surface mapping collected using the system of FIG. 1, according to various embodiments. As described in more detail in reference to FIG. 1, the system 100 is configured to receive the treatment design 200 and to generate an exposure pattern. As part of the operations of the system 100, the treatment design 200 can be projected onto a 3D mapping of the portion of the user's body (e.g., volume of hair 120 of FIG. 1), The 3D model includes several reference points 212 in the form of corresponding triangles of a mesh structure, although other polygon shapes are also contemplated.

Generating the 3D projection 210 can include multiple computational operations to generate a numerical representation of a portion of the hair and/or face of the user using the camera (e.g., a surface 3D mapping). The camera can be or include multiple image sensors configured to capture stereoscopic images. In this way, the numerical representation of the portion of the hair and/or face can be or include a tensor of position information defining a surface of the volume of hair 120. Examples of computational techniques include edge-detection, feature or point detection and tracking, and/or point-cloud methods. For example, the system 100 can be configured with a time-of-flight camera, with LiDAR systems, or with stereoscopic cameras, such that the facial mapping can represent a surface generated by contours connecting points and/or features. Flyover techniques employing visual simultaneous localization and mapping (vSLAM) can be used to generate a surface model of the volume of hair 120 and/or the entire head and face. In some embodiments, the system 100 can include an implementation of machine learning, such as a face detection/mapping module that can be trained to predict the mapping based on a subset of features and/or points measured by the camera. In this way, the system 100 can be configured to reduce the number of measurements used to generate the mapping, which can improve system performance, for example, by reducing the length of time used to capture images of the user's hair and face.

Other adaptations can be performed for variations in lighting conditions, viewing angles, or other factors. As one example, a light sensor mounted on the hair contouring device 104 can be used to measure current lighting conditions relative to a baseline lighting condition. If the environment is too bright or too dark, the hair contouring device 104 can generate a prompt to increase illumination and/or can activate a radiation source (e.g., radiation source 108 of FIG. 1) that can or be appreciably invisible to the subject (e.g., an infrared source to provide invisible illumination). In some embodiments, the hair contouring device 104 can provide feedback to a user (e.g., via synthesized voice cues or visual indications) to adjust the lighting conditions for better results. In some embodiments, the system can generate feedback to instruct the user to reposition relative to the camera(s) (e.g., generating a prompt to reposition the user's face from a face-on to a side-on position). It should be understood that described embodiments are capable of implementation in many possible ways to determine matches between captured image data and texture data in a 3D model, including matching detected edges or contours, color/pixel values, depth information, or the like in different combinations, and at particular threshold levels of confidence, any of which can be adjusted based on lighting conditions, user preferences, system design constraints, or other factors.

The projection 210 can be generated by various means to reduce artifacts of the projection onto the face. For example, the polygons into which the design 200 is divided can be heterogeneously scaled, skewed, or otherwise modified when generating the projection 210, as illustrated. For example, where the treatment design 200 can include each polygon with a uniform size, the projection 210 can include many different sizes for the polygons 212. In some embodiments, resizing can correspond to the contours of the mapping, where regions of high dynamic range correspond to smaller polygons 212 and regions of low dynamic range correspond to larger polygons 212. Additionally and/or alternatively, the projection 210 can be resized in accordance with information density. For example, where the number of polygons 202 making up the treatment design 200 correspond to the resolution of the design, analogous to a pixel resolution of a digital image, information-dense regions of the design 200 can include relatively high numbers of polygons 202, compared to regions that include relatively sparse design information. As an illustrative example, more polygons can be used to describe textured hair including curls, frizz, or waves, in contrast to regions of straight hair.

The exposure data illustrated in FIG. 2B can be generated by taking into account the intensity values of each material channel included in the design 200, as well as exposure kinetics data for the photo-responsive materials. For example, treatment values for a first polygon 212-1, as indicated by the intensity data of the design 200, can be effected by exposing the first polygon to the multiple distinct wavelength channels (e.g., $\lambda_{1-4}$) for different durations corresponding to the characteristic chemical kinetics of the different materials. In some embodiments, a "wipe" operation can be implemented by exposing the photo-responsive materials to a neutralization or breakdown-wavelength. In some embodiments, photo-responsive materials undergo irreversible polymerization, isomerization, or shape-change transformations under illumination at one or more of the distinct wavelength channels. Through use of biocompatible and non-toxic photo-responsive materials, the contouring treatment can be temporary, with little to no deleterious effect on the hair or skin.

In some embodiments, the treatment design 200 can be adapted using data collected during mapping operations to determine contouring treatments targeting one or more regions of hair of the user (e.g., volume of hair 120 of FIG. 1). In this way, using depth information, edges, and/or other features, the treatment design 200 can incorporate specific features and configurations of illumination. In an illustrative example, a template treatment design can be received by the system and can be adjusted to include treatment information addressing non-uniform hair structure, such as where the volume of hair 120 exhibits irregular curls, frizz, waves, straightness, etc. As such, the projection of the treatment design 200 onto the face mapping 210 can include adaptive mesh sizing and treatment levels, corresponding to identification of features and/or treatment regions. In some embodiments, the features and/or treatment regions can be manually indicated, for example, by using a visibly-transparent fluorescent marker or other indicator that can be detected by optical sensors (e.g., UV absorbing ink, IR absorbing ink, etc), which can be used to indicate a specific treatment location, for example, by associating a specific indicator with a specific treatment. In an illustrative example, a UV-visible-NIR-IR image sensor system (e.g., camera(s) 150 of FIG. 1) can be used to detect two or more types of indicators for surface treatments, where a first indicator is associated with expansion treatment and a second indicator is associated with contraction treatment.

Figure 3:
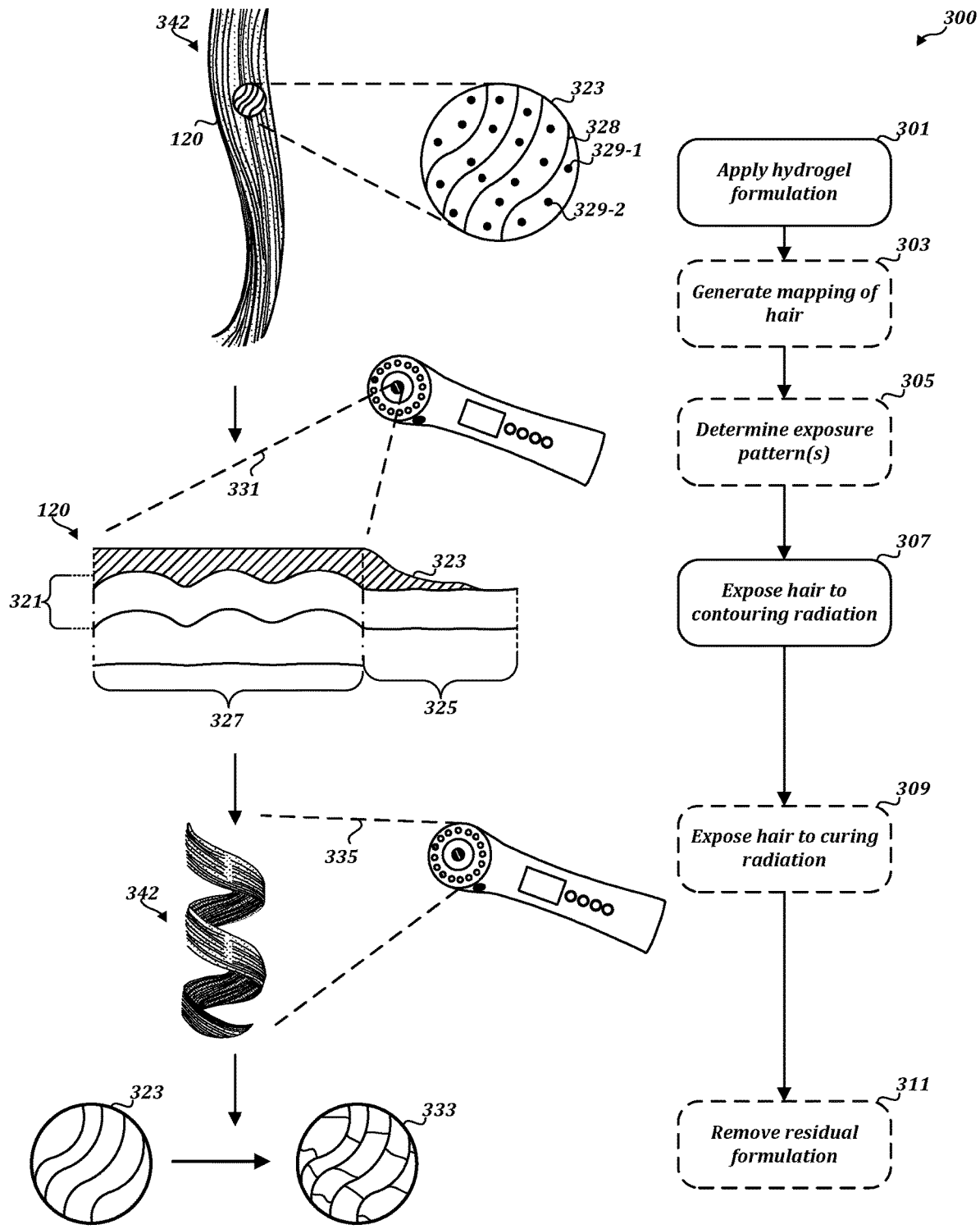
FIG. 3 is a schematic diagram illustrating an example technique for contouring a volume of hair using photo-responsive materials, in accordance with various embodiments.

FIG. 3 is a schematic illustration of an example contouring technique 300 using photo-responsive materials, in accordance with various embodiments. The individual operations of the example treatment 300 can be implemented by the system 100 of FIG. 1. As such, the example treatment 300 is described as part of an example flow implemented by a computer system and a computer-controlled illumination system (e.g., client computing device 104 of FIG. 1). In this way, the example treatment 300 can be stored as computer-executable instructions on a non-transitory computer-readable memory that, when executed by one or more processors of the client computing device 104, can implement the operations of the flow illustrated in FIG. 3. It is understood that other systems and methods are contemplated, of which FIG. 3 describes but one example.

At operation 301, the example contouring technique 300 includes providing a photo-responsive hydrogel formulation 323 to the volume of hair 120. Providing can include applying the material manually or using other approaches, including but not limited to rinsing, spraying, or other application technique. For surface treatments, contouring can be kept within the outer layers 321 of the hair 120, such that topical application of the photo-responsive hydrogel formulation 323 can be used to apply the example technique 300, without liberally applying the photo-responsive hydrogel formulation 323 to the entire volume of hair 120.

In some embodiments, the example technique 300 optionally includes identifying the volume of hair 120 as part of generating a mapping of the hair at operation 303. As described in more detail in reference to FIG. 2A-2B, a contouring treatment design can be or include a general contouring treatment based on a template. For example, aggregate data for images matched to a user's age, ethnicity, sex, or the like, can be used to identify and/or receive contouring treatment design templates, from which a system can include specific treatments based on hair mapping of the user. In some embodiments, by contrast, the example treatment 300 can begin directly with mapping the hair and/or face of the user, rather than working from a template. Advantageously, initializing treatment with operation 301 directly, rather than modifying a template design, can facilitate spot treatments and can reduce the time and computational resources involved in applying contouring treatments. In some embodiments, the example contouring technique 300 can include identifying multiple regions of skin including the volume of hair 120. For example, treatment can include applying symmetric effects to opposing sides of a face (e.g., subject's face 102 of FIG. 1). In this way, the example contouring technique 300 can include, at operation 301, identifying more than one volume of hair 120 to apply contouring treatments.

In some embodiments, example technique 300 optionally includes determining one or more exposure patterns 327 at operation 305. The one or more exposure patterns 327 can include a partial treatment of the volume of hair 120, such that a portion of the hair is exposed to actuating radiation, while a peripheral region 325 remains untreated. The exposure patterns 327 correspond to one or more types of shape, morphology, and/or chemical modification of the photo-responsive hydrogel formulation 323, as described in reference to FIG. 2A and FIG. 2B. For example, determining the exposure patterns 327 can include projecting a treatment design (e.g., treatment 200 of FIG. 2A) onto a mapping of a target body surface (e.g., projection 210 of FIG. 2B). Determining the exposure patterns 327 can also include detecting one or more features on the volume of hair 120 and modifying the treatment design onto a mapping of the volume of hair 120. Still further, determining the exposure patterns 327 can include directly mapping the volume of hair 120, classifying features detected on the volume of hair 120, and identifying the exposure patterns 327 using the classification. In an illustrative example, classification can include using a machine-learning model trained to classify images or other surface data (e.g., stereoscopic, multispectral and/or surface mapping data) into one or more of a number of possible feature classes. The training can include unsupervised learning processes, whereby the classifier is provided with a training set of images of the relevant modality, such that it optimizes an objective function (e.g., nearest neighbor, Euclidean distance, etc.) and is thereby configured to classify hair shapes, types, or forms with confidence. Additionally and/or alternatively, feature detection can be provided to the user via a display element (e.g., interface elements 110 of FIG. 1) to confirm and/or provide a classification of the feature. For example, the display can highlight features and, corresponding to the type of photo-responsive hydrogel formulation 323 applied, can receive feedback from the user identifying the type of treatment to be applied to each respective feature.

As described in more detail in reference to FIG. 2B, the exposure patterns 327 can be or include a tensor of exposure data describing one or more types of treatments (surface, volumetric, aesthetic, etc.). In this way, the exposure patterns 327 can include timing and spatial information for one or more photo-responsive hydrogel formulations 323. In the example of contouring technique 300, the photo-responsive hydrogel formulation 323 can be or include one or more constituent materials that expand when exposed to a first characteristic wavelength and contract when exposed to a second characteristic wavelength. Further, the expansion and contraction can be characterized by differing kinetic parameters (e.g., polymerization rate) and/or the exposure patterns 327 can be of differing sizes, such that the exposure pattern can include spatial localization and timing information relating to one or more radiation sources (e.g., radiation source(s) 108 of FIG. 1). In this way, the expansion treatments can be effected by a first radiation source 108-1, while the contraction treatments can be effected by a second radiation source 108-2, according to the exposure patterns 327 for the volume of hair 120. It is to be understood that example treatment 300 is not a limiting example. In some embodiments, contraction and expansion is applied in different manners, or can be applied alone. For example, more than two radiation sources 108 can be used, such that a contouring design can include contraction, as well as other types of shape, morphology, or chemical change can be applied. The photo-responsive hydrogel formulation 323, when cured using the fixing source 108-2, can be set into the configuration resulting after exposure. Even so, after curing, the photo-responsive hydrogel formulation 323 can remain soft and flexible.

At operation 307, the volume of hair 120 is exposed to contouring radiation 331 at the exposure patterns 327, as part of effecting the example technique 300. As shown, the exposure can be such that the photo-responsive hydrogel formulation 323 can undergo a chemical change, such as a photo-initiated isomerization, resulting in an isotropic volumetric expansion or an isotropic volumetric contraction that, when applied to the volume of hair 120, flexes or strains the volume of hair 120 from a straight or waved shape 340 to a curled shape 342. The photo-responsive hydrogel formulation 323 can be or include a hydrogel monomer that forms a crosslinked hydrogel in response to irradiation from the radiation sources 108.

The hydrogel formulation 323 can be or include, but is not limited to, gelatin methacryloyl (Gel-MA), hydroxyethylmethacrylate (HEMA), ethylene glycol diacrylate (EGDA), or poly(ethylene glycol) diacrylate, poly(N-isopropylacrylamide) (pNIPAAm) hydrogel. In some embodiments, the photo-responsive hydrogel formulation 323 can also include a synthetic polymer. In some embodiments, the photo-responsive hydrogel formulation 323 can include a stiffener, including, but not limited to calcium carbonate. In some embodiments, the photo-responsive hydrogel formulation 323 can further include a photo-initiator. The photoinitiator can be characterized by two-photon absorption in the near-infrared (NIR) spectral range, defined from about 750 nm to about 1400 nm, such that the radiation sources 108 can be or include NIR sources. The photoinitiator can be or include a first type of particles 329-1, such as upconversion nanoparticles, suspended in the hydrogel formulation 323, including, but not limited to titanium oxide nanoparticles. The photoinitiator can be or include one or more water-soluble, biodegradable, and/or cytocompatible photoinitiators, such as 2,2'-Azobis[2-methyl-N-(2-hydroxyethyl)propionamide] (CAS Number: 61551-69-7), Lithium phenyl-2, 4,6-trimethylbenzoylphosphinate (CAS Number 85073-19-4), or Eosin-Y. In some embodiments, the photoinitiator can be or include a combination of eosin Y, triethanolamine, and 1-vinyl-2-pyrrolidinone. In some embodiments, the hydrogel formulation 323 is actuated at least in part by heat, such that the hydrogel formulation 323 can include a second type of particle 329-2, such as chromium oxide and/or iron oxide particles, dispersed in the hydrogel formulation 323.

To apply isotropic strain on the volume of hair 120, hydrogel formulation 232 can include photo-responsive filaments 328. The photo-responsive filaments 328 can include surface moieties to molecularly bond or otherwise adsorb with individual hairs of the volume of hair 120 and align with the hairs. In this way, absorption of contouring radiation 331 at the outer layers 321 of the volume of hair 120 can induce anisotropic strain on the hairs, forming curls, or conversely, forcibly straightening the volume of hair 120. To that end, the example technique 300 can be equally applied to curl or to straighten the volume of hair 120, depending at least in part on the composition of the hydrogel formulation 323 and/or the energy of the contouring radiation 331, as described in more detail in reference to FIG. 4.

At operation 309, the example technique 300 includes exposing the volume of hair 120 to curing radiation 335, as part of fixing the hair in the curly state 342. Exposure of the hydrogel formulation 323 to curing radiation 335 can induce one or more chemical, structural, or morphological changes, resulting in preserving the conformational change induced during exposure to the contouring radiation 331 at operation 307. Curing radiation 335 can induce, for example, cross-linking of the hydrogel formulation 323 to form a cross-linked hydrogel formulation 333. In addition to, or in alternative to, cross-linking, the curing radiation 335 can induce a temporary vitrification of the hydrogel formulation 323, such that the hydrogel formulation 323 does not form covalent crosslinked bonding, but rather increases in intermolecular bonds or otherwise increases in viscosity to fix the volume of hair 120 at least temporarily in place. In some embodiments, the hydrogel formulation 323 further includes a chemical material that cross-links in response to ultraviolet photons from ambient sunlight, such that the curing radiation 335 is provided without use of the hair contouring device 104. Further still, the hydrogel formulation 323 can include constituent materials that crosslink or otherwise cure in response to humidity, carbon dioxide, oxygen, or other components of atmospheric air. In this way, curing at operation 309 can be effected at night, without exposure to ambient sunlight or to curing radiation 335 generated by radiation source(s) 108.

Subsequent to exposing the photo-responsive hydrogel formulation 323, the example treatment 300 can optionally include removing residual photo-responsive hydrogel formulation 323 at operation 311. Removing residual material can also include removing excess treated material 333. The force applied to the volume of hair 120 by the treated material can effect a morphological change from one hair type to another hair type, such as from straight to wavy or from curly to straight, consistent with a contouring treatment. Where the photo-responsive hydrogel formulation 323 is water-soluble, the treated material 333 can be water resistant. In this way, removal of residual material can include techniques available without specialized equipment or training, such as rinsing the volume of hair 120.

Figure 4:
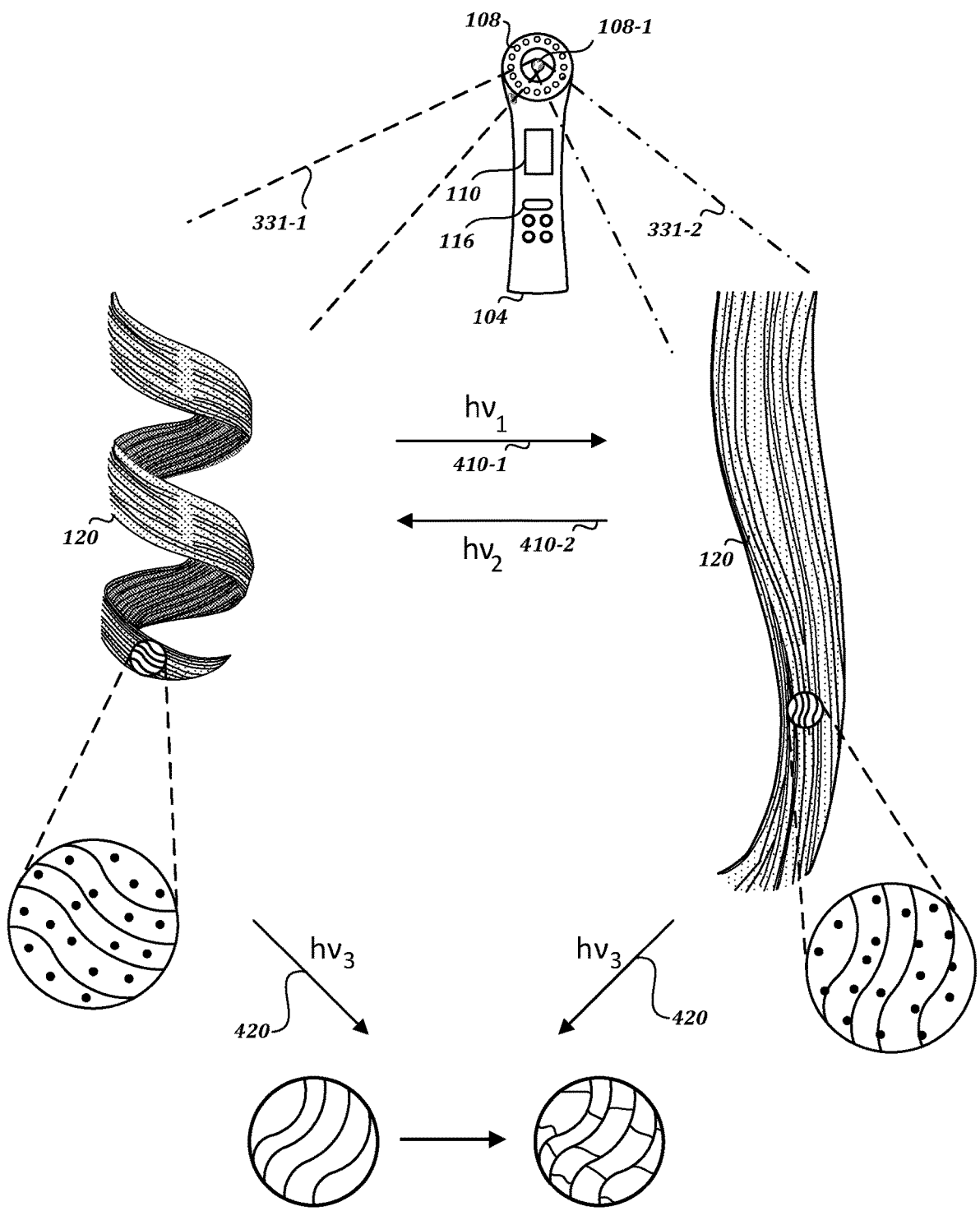
FIG. 4 is a schematic diagram illustrating reversible contouring and irreversible contouring of a volume of hair, in accordance with various embodiments.

FIG. 4 is a schematic diagram illustrating reversible contouring and irreversible curing of the volume of hair 120, in accordance with various embodiments. In the illustrative embodiments shown, the hair contouring device 104 is employed to reversibly contour the volume of hair 120 by exposing the volume of hair 120 to contouring radiation 331, and subsequently to fix the volume of hair 120 by exposing the volume of hair 120 to curing radiation 335. In this way, the techniques illustrated in FIG. 4 are exemplary embodiments of the example technique 300 of FIG. 3. As described in more detail in reference to FIG. 3, reversible contouring can be implemented using a targeted approach and/or using a general approach. In this context, the targeted approach refers to the mapping and exposure techniques described in reference to FIGS. 1-3. By contrast, the general approach refers to manual control of the hair contouring device 104 through user interaction with the input component(s) 116 to activate radiation sources 108 and manually guide the exposure of the volume of hair 120. To simplify the explanation of the techniques of FIG. 4, description focuses on the general approach, but it is understood that the photo-chemical changes induced in the hydrogel formulation 323, and the consequent morphological changes in the volume of hair 120, are equally applicable to both targeted and general approaches.

In some embodiments, the contouring source 108-1 generates the contouring electromagnetic radiation 331 within a first energy range 410 to induce a conformation change of the hydrogel formulation 323. The first energy range 410 can correspond to near-ultraviolet wavelengths from about 300 nm to about 400 nm, or about 3.0 eV to about 4.2 eV. The first energy range 410 can correspond to near-infrared wavelengths from about 750 nm to about 1400 nm, or about 800 meV to about 1.7 eV. The first energy range 410 can correspond to visible wavelengths from about 400 nm to about 750 nm, or about 3.0 eV to about 4.2 eV. In this context, the term about corresponds to a value within 10% of the stated value. In some embodiments, different contouring sources 108-1 are included as part of the hair contouring device 104 to facilitate different conformation changes. For example, the hydrogel formulation 323 can be characterized by different photo-responsive conformation changes in response to different contouring radiation 331 energies. For example, a first energy range 410 for straightening, corresponding to volumetric expansion of the hydrogel formulation 323 or to straightening of the filaments 328, could be centered around a first discrete wavelength 410-1. In contrast, a first energy range 410 for curling, corresponding to volumetric contraction of the hydrogel formulation 323 or to curving of the filaments 328, could be centered around a second discrete wavelength 410-2. The energy or wavelength employed for each morphological change can correspond to the chemical structure of the hydrogel formulation 323.

In an illustrative example, the hydrogel formulation 323 can include filaments 328 of poly(NIPAm-coacrylic acid-co-spiropyran) including a spiropyrane moiety. In an aqueous hydrogel, the filaments 328 can spontaneously assume a curved shape. Photoisomerization of the spiropyrane moiety in a hydrogel polymer under exposure to visible wavelength photons can induce a morphology change that straightens the filaments 328. In this way, the combined effect of many filaments 328 can straighten the volume of hair 120. In this example, the morphology change of the hydrogel formulation 323 is spontaneously reversible while the volume of hair 120 is wet, without a second exposure to contouring radiation 331.

In another illustrative example, the hydrogel formulation 323 can include poly(NIPAm) within which a light-absorbing material is dispersed, such as chromium oxide, iron oxide, or another type of oxide particle. Under exposure to visible wavelength photons, the hydrogel formulation 323 can swell, facilitated by a photo-thermal conversion at the light-absorbing material. Under exposure to ultraviolet wavelength photons, such as near-ultraviolet photons, the hydrogel formulation 323 can undergo a volumetric contraction that reverses the expansion under visible wavelength photons. Similarly to the filament example above, providing a hydrogel formulation 323 of a poly(NIPAm-coacrylic acid-co-spiropyran) hydrogel can replace the ultraviolet wavelength photo-transition with a spontaneous reverse pathway in the presence of water molecules.

In light of the spontaneous nature of some shape changes in the presence of water molecules, the curing radiation 335 permits the volume of hair 120 to be fixed in a particular conformation. To facilitate curing, the hydrogel formulation 323 can include photo-responsive moieties, monomers, or other constituent components, that can crosslink in response to exposure to the curing radiation 335 within a second energy range 420. For example, the hydrogel formulation 323 can absorb ultraviolet wavelength photons and irreversibly crosslink to form a stable structure. The second energy range 420 can correspond to near-ultraviolet wavelengths, visible wavelengths, or near-infrared wavelengths, in accordance with the photo-chemical energy sensitivity of the hydrogel formulation 323. For example, the hydrogel formulation 323 can include a covalently crosslinked hydrogel with additional, reversibly light-responsive crosslinking points based on host-guest interaction. A non-limiting example of such a structure includes α-CD-modified acrylamide, azobenzene acrylamide and methylene bisacrylamide crosslinker. Under exposure to visible wavelength photons, the trans-azobenzene and α-CD moieties form crosslinks due to host-guest interactions, which can be reversed under exposure to ultraviolet wavelength photons. In this way, the second energy range 420 can correspond to the visible wavelength range, such that curing radiation 335 can be provided by ambient sunlight or by radiation sources 108.

To reduce the likelihood that contouring radiation 331 induces photo-curing of the hydrogel formulation 323, or that curing radiation 335 induces a morphology change of the hydrogel formulation 323, the first energy range 410 and the second energy range 420 can be non-overlapping. In this context, the term "non-overlapping" describes a condition where a negligible portion of the energy distribution functions of each respective energy range overlap. For example, where each type of radiation source 108 is a monochromatic "line" source, the emission of photons can be described by an energy distribution centered around a central wavelength. For ultraviolet wavelength sources, the central wavelength can be, but is not limited to, about 365 nm. For visible wavelength sources, the central wavelength can be, but is not limited to, about 430 nm. As such, non-overlapping ranges would be characterized by little to no emission in common at a wavelength of about 400 nm, between the two central wavelengths, such that activating the contouring source(s) 108-1 using input component(s) 116 does not induce photo-curing, activating curing source(s) 108-3 using input components 116 does not induce contouring, and the constituent operations of the example technique 300 of FIG. 3 can be isolated.

It is understood that energy distributions can be described by a "full width at half maximum" (FWHM). In the case of radiation sources 108 where the contouring source(s) 108-1 and the curing source(s) 108-3 respectively correspond to neighboring spectral ranges, such as near-ultraviolet and visible wavelength ranges, an example of "non-overlapping" can include a configuration of radiation sources 108 such that the FWHM of the contouring source(s) 108-1 does not overlap in terms of wavelength with the FWHM of the curing source(s) 108-3. The second type of contouring source 108-2 can also be non-overlapping with the contouring source(s) 108-1 and the curing source(s) 108-3, to optically isolate the effects of each respective photo-chemical modification of the hydrogel formulation 323. In the illustrative example described above, where the central wavelength of the visible wavelength source is about 430 nm and the ultraviolet source is about 365 nm, the FWHM of each respective source can be up to or about 10 nm, up to or about 20 nm, up to or about 30 nm, up to or about 40 nm, up to or about 50 nm, including fractions or interpolations thereof, without significant overlap between sources, assuming a typical gaussian photon energy distribution.

In some embodiments, the hydrogel formulation can later be removed through rinsing with water, as the cured hydrogel formulation 333 can be water soluble, as described in more detail in reference to FIG. 3. For example, in the case of the host-guest interactions between azobenzene and α-CD moieties, reversible cross-linking can permit the cured hydrogel formulation 333 to be de-crosslinked and subsequently removed.

Figure 5:
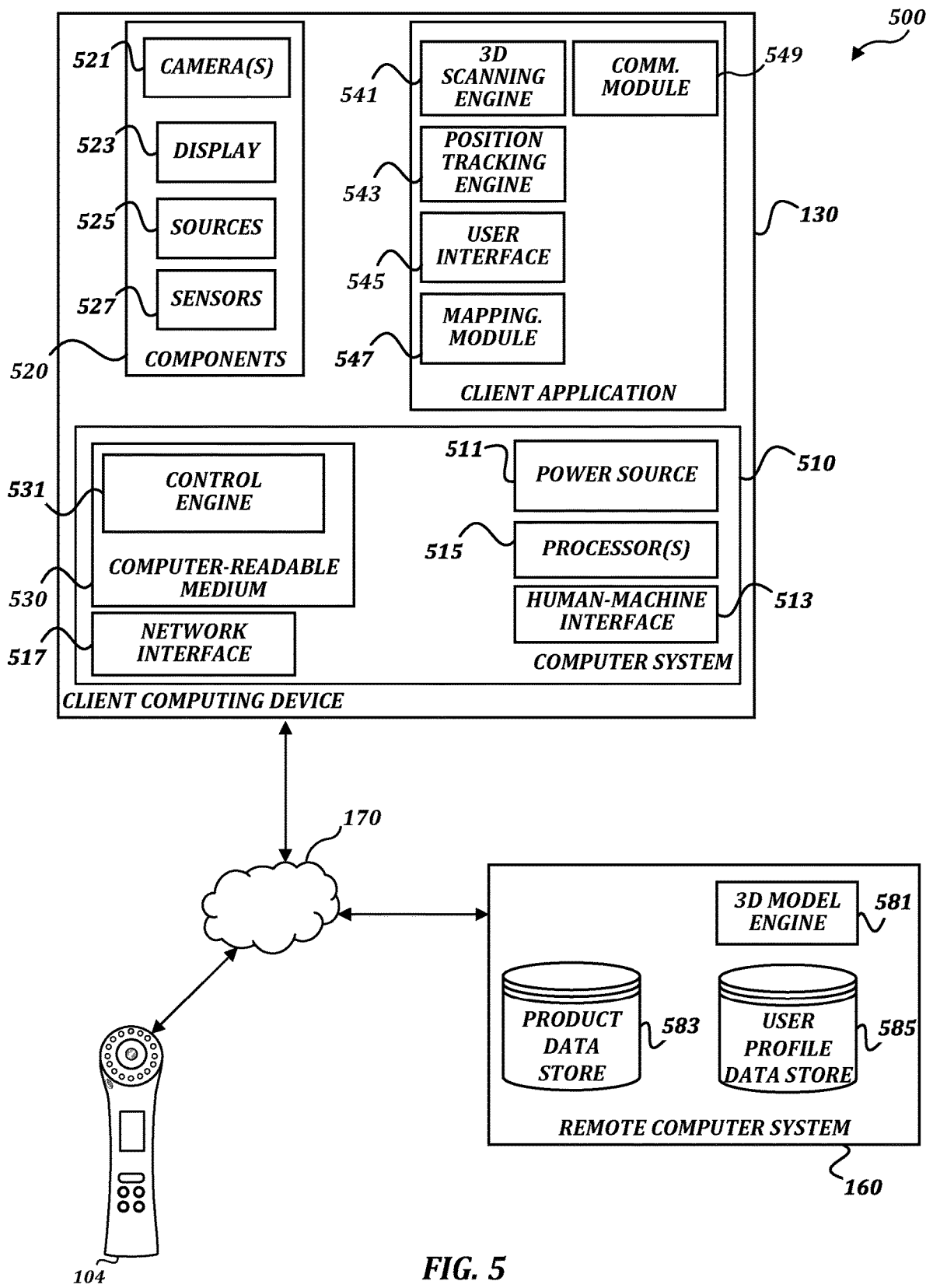
FIG. 5 is a block diagram that illustrates an example system, including components of the system of FIG. 1, in accordance with various embodiments.

FIG. 5 is a block diagram that illustrates an example system 500, including components of the system of FIG. 1, in accordance with various embodiments. The example system 500 includes the client computing device 130 in electronic communication (e.g., over network 170) with the remote computer system 160. Example system 500 illustrates an example of the system 100 of FIG. 1, in a context of associated system elements, and, as such, describes electronics and software executing operations as described in reference to FIGS. 1-4. FIG. 5 depicts a non-limiting example of system elements, features and configurations. Many other features and configurations are contemplated. In the example shown in FIG. 5, the client computing device 130 of FIG. 1 includes a computer system 510, multiple components 520 for interacting with the biological surface 102 and the volume of hair 120, a computer-readable medium 530, and a client application 540, that can be stored as computer-executable instructions on the computer-readable medium 530, and, when executed by the computer system 510, can implement the operations described in reference to the system 100 of FIG. 1, and the operations of the example techniques of FIGS. 2A-4.

The client computing device 130 incorporates subcomponents including, but not limited to, a power source 511, a human-machine interface 513, one or more processors 515, a network interface 517, and can include the computer-readable medium 530. The power source 511 is a direct-current power source, for example, a rechargeable battery or a rectified power supply configured to connect to line-power (e.g., 110 VAC, 220 VAC, etc.). The human-machine interface (HMI) 513 can include any type of device capable of receiving user input or generating output for presentation to a user, such as a speaker for audio output, a microphone for receiving audio commands, a push-button switch, a toggle switch, a capacitive switch, a rotary switch, a slide switch, a rocker switch, or a touch screen.

The one or more processors 515 are configured to execute computer-executable instructions stored on the computer-readable medium 530. In an embodiment, the processor(s) 515 are configured to receive and transmit signals to and/or from the components 520 via a communication bus or other circuitry, for example, as part of executing the client application 540. The network interface 517 is configured to transmit and receive signals to and from the client computing device 130 (or other computing devices) on behalf of the processors 515. The network interface 517 can implement any suitable communication technology, including but not limited to short-range wireless technologies such as Bluetooth, infrared, near-field communication, and Wi-Fi; long-range wireless technologies such as WiMAX, 2G, 3G, 4G, LTE, and 10G; and wired technologies such as USB, Fire-Wire, Thunderbolt, and/or Ethernet. The computer-readable medium 530 is any type of computer-readable medium on which computer-executable instructions can be stored, including but not limited to a flash memory (SSD), a ROM, an EPROM, an EEPROM, and an FPGA. The computer-readable medium 530 and the processor(s) 515 can be combined into a single device, such as an ASIC, or the computer-readable medium 530 can include a cache memory, a register, or another component of the processor 515.

In the illustrated embodiment, the computer-readable medium 530 stores computer-executable instructions that, in response to execution by one or more processors 515, cause the client computing device 130 to implement a control engine 531. The control engine 531 controls one or more aspects of the client computing device 130, as described above. In some embodiments, the computer-executable instructions are configured to cause the client computing device 130 to perform one or more operations such as generating a surface mapping of the volume of hair 120, projecting a contouring design onto the mapping, and determining exposure patterns 327. In some embodiments, the control engine 531 controls basic functions by facilitating interaction between the computer system 510 and the components 520 according to the client application 540. In some embodiments, the control engine 531 detects input from HMI 513 indicating that a contouring routine is to be initiated (e.g., in response to activation of a power switch or "start" button of the input components 116, or detection of a face in front of the camera 140 of FIG. 1), or receives signals from client computing device(s) 130, the remote computer system 160, or user device(s) 190 (e.g., over a Bluetooth paired connection).

The components of the client computing device 130 can be adapted to the application or can be specific to the application (e.g., ASICs). For example, the components 520 can include one or more cameras 521, a display 523, one or more radiation sources 525, and/or one or more radiation sensors 527, as described in more detail in reference to FIG. 1. In some embodiments, the components 520 are integrated into a single device. In this way, the client computing device 130 can be a specialized computing device, configured to execute the client application 540 in coordination with the components 520. In some embodiments, the client computing device 130 is a general purpose mobile electronic device, such as a tablet or smartphone, storing the client application 540.

In some embodiments, the client application 540 also includes an image capture/3D scanning engine 541 configured to capture and process digital images (e.g., color images, infrared images, depth images, etc.) obtained from one or more of the components 520 including but not limited to stereoscopic images, LiDAR data, or other forms of surface/depth sensing information. In some embodiments, such data are used to obtain a 3D contour mapping of the target surface (e.g., volume of hair 120 of FIG. 1). In some embodiments, the digital images or scans are processed by the client computing device 130 and/or transmitted to the remote computer system 160 for processing in a 3D model engine 581. In an embodiment, captured image data is used in position tracking engine 543 for determining the position of features, key-points, or edges on the biological surface 102 to facilitate tracking of the volume of hair 120. In some embodiments, the position tracking engine 543 tracks the contours of the target surface in a 3D space, for example, by implementing v-SLAM techniques. In some embodiments, position information from the position tracking engine 543 is used to generate signals to be transmitted to the control engine 531, which are used to control one or more components 520 or elements of the computer system 510 including, for example, the sources 525 or the HMI 513, according to techniques described herein. In some embodiments, digital 3D models described herein are generated based on sensor data obtained by the client computing device 130. As such, the digital 3D models are generated by the client computing device 130 or some other computing device, such as a cloud computing system, or a combination thereof.

In some embodiments, the client application 540 includes a user interface 545. In an embodiment, the user interface 545 includes interactive functionality including but not limited to graphical guides or prompts, presented via the display to assist a user in selecting contouring treatments, tutorial videos, or animations. In some embodiments, the user interface 545 provides guidance (e.g., visual guides such as arrows or targets, progress indicators, audio/haptic feedback, synthesized speech, etc.) to guide a user under particular lighting conditions, angles, etc., in order to ensure that sufficient data is collected for use by mapping and projection engines. The user interface 545 can also be used to navigate to and/or through a catalogue of hair contouring designs, available from a social media platform, content network, or other source, for example, through a digital browser environment. In this way, the techniques described in reference to FIGS. 1-4 can include selecting a hair contouring design using the client computing device 130 and receiving, by the hair contouring device 104, the hair contouring design via communication circuitry configured to pair with the client computing device. In some embodiments, the input components 116 are integrated as part of the HMI 513 and/or the user interface 545, such that the input component(s) can be physical controls or "soft" controls implemented on a tactile display or through voice interaction. For example, the inputs provided to the hair contouring device 104 can be or include, but are not limited to, a user actuation of a button or switch, a screen tap on the user interface 110, and/or a voice command (e.g., "fix hair now").

The client application 540 can include a mapping module 547. The mapping module 547 can be or include computer-readable instructions (e.g., software, drivers, etc.) for projecting a numerical representation of a contouring treatment design onto the volume of hair 120. As part of the operation of the mapping module 547, the client application 540 can receive real-time data from the camera(s) 521 and sensors 527, which can be processed by the 3D scanning engine 541 and the position tracking engine 543. In this way, the mapping module 547 can respond to motion of the target body surface, thereby increasing the tolerance of the client computing device 130 for motion on the part of the user without loss of fidelity of the contouring treatment. In some embodiments, the computational resource demand for such real time scanning/tracking, can be spread across multiple devices, such as the remote computer system 160, through parallelization or distribution routines.

A communication module 549 of the client application 540 can be used to prepare information for transmission to, or to receive and interpret information from other devices or systems, such as the remote computer system 160 or the user device(s) 190, As described in more detail in reference to FIG. 1. Such information can include captured digital images, scans, or video, personal care device settings, custom care routines, user preferences, user identifiers, device identifiers, or the like. In an embodiment, the client computing device 130 collects data describing execution of contouring routines, image data of body surfaces, or other data. In an embodiment, such data is transmitted via the network interface 517 to the remote computer system 160 for further processing or storage (e.g., in a product data store 583 or user profile data store 585). The client computing device 130 can be used by a consumer, personal care professional, or some other entity to interact with other components of the system 500, such as the remote computer system 160 or user device(s) 190. In an embodiment, the client computing device 130 is a mobile computing device such as a smartphone or a tablet computing device equipped with the components 520 and the client application 540 or provided with the components through electronic coupling with a peripheral device.

The remote computer system 160 can include one or more server computers that implement one or more of the illustrated components, e.g., in a cloud computing arrangement. The remote computer system 160 can include a projection engine 587, the 3D model engine 581, the product data store 583, and the user profile data store 585. In an embodiment, the 3D model engine 581 uses image data (e.g., color image data, infrared image data) and depth data to generate a 3D model of the target body surface. The image data is obtained from the client computing device 130, for example, from the camera(s) 521 or the sensor(s) 527 that are integrated with or otherwise electronically coupled with client computing device 130. In an embodiment, image data and depth data associated with a user is stored in the user profile data store 585. In an embodiment, user consent is obtained prior to storing any information that is private to a user or can be used to identify a user.

In an embodiment, the mapping/projection engine 587 performs processing of data relating to a contouring routine, such as generating mappings of target surfaces using image/sensor data. In some embodiments, the projection engine 587 generates contouring treatment data using user information from the user profile data store 585, the product data store 583, the 3D model engine 581, or some other source or combination of sources.

The 3D model engine 581 can employ machine learning or artificial intelligence techniques (e.g., template matching, feature extraction and matching, classification, artificial neural networks, deep learning architectures, genetic algorithms, or the like). For example, to generate the contouring treatment in accordance with a surface mapping of a face and hair, the 3D model engine 581 can analyze a facial mapping generated by the 3D model engine 581 to determine head-shape and predict hair volume under the outer layers 321. The 3D model engine 581 can receive data describing a contouring treatment based on an identifier code provided by the user through the client computing device(s) 130. In such a scenario, the 3D model engine 581 can use such information to generate a projection of the contouring treatment design onto the 3D mapping of the volume of hair.

The devices shown in FIG. 5 can communicate with each other via the network 170, which can include any suitable communication technology including but not limited to wired technologies such as DSL, Ethernet, fiber optic, USB, Firewire, Thunderbolt; wireless technologies such as WiFi, WiMAX, 3G, 4G, LTE, 5G, 10G, and Bluetooth; and private networks (e.g., an intranet) or public networks (e.g., the Internet). In general, communication between computing devices or components of FIG. 5, or other components or computing devices used in accordance with described embodiments, occur directly or through intermediate components or devices.

Alternatives to the arrangements disclosed and described with reference to FIGS. 1-5, are possible. For example, functionality described as being implemented in multiple components can instead be consolidated into a single component, or functionality described as being implemented in a single component can be implemented in multiple illustrated components, or in other components that are not shown in FIGS. 1-5. As another example, devices in FIGS. 1-5 that are illustrated as including particular components can instead include more components, fewer components, or different components without departing from the scope of described embodiments. As another example, functionality that is described as being performed by a particular device or subcomponent can instead be performed by one or more other devices within a system. As an example, the 3D model engine 514 can be implemented in the client computing device(s) 130 or in some other device or combination of devices.

In addition to the technical benefits of described embodiments that are described elsewhere herein, numerous other technical benefits are achieved in some embodiments. For example, the system 500 allows some aspects of the process to be conducted independently by personal care devices or client computing devices, while moving other processing burdens to the remote computer system 160 (which can be a relatively high-powered and reliable computing system), thus improving performance and preserving battery life for functionality provided by personal care devices or client computing devices.

In general, the word "engine," as used herein, refers to logic embodied in hardware or software instructions written in a programming language, such as C, C++, COBOL, JAVA™, PHP, Perl, HTML, CSS, JavaScript, VBScript, ASPX, Microsoft .NET™, and/or the like. An engine can be compiled into executable programs or written in interpreted programming languages. Software engines can be callable from other engines or from themselves. Generally, the engines described herein refer to logical modules that can be merged with other engines or divided into sub-engines. The engines can be stored in any type of computer-readable medium or computer storage device and be stored on and executed by one or more general purpose computers, thus creating a special purpose computer configured to provide the engine or the functionality thereof.

As understood by one of ordinary skill in the art, a "data store" as described herein can be any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries can be used, and the computing device can be accessible locally instead of over a network, or can be provided as a cloud-based service. A data store can also include data stored in an organized manner on a computer-readable storage medium, as described further below. One of ordinary skill in the art will recognize that separate data stores described herein can be combined into a single data store, and/or a single data store described herein can be separated into multiple data stores, without departing from the scope of the present disclosure.

Figure 6:
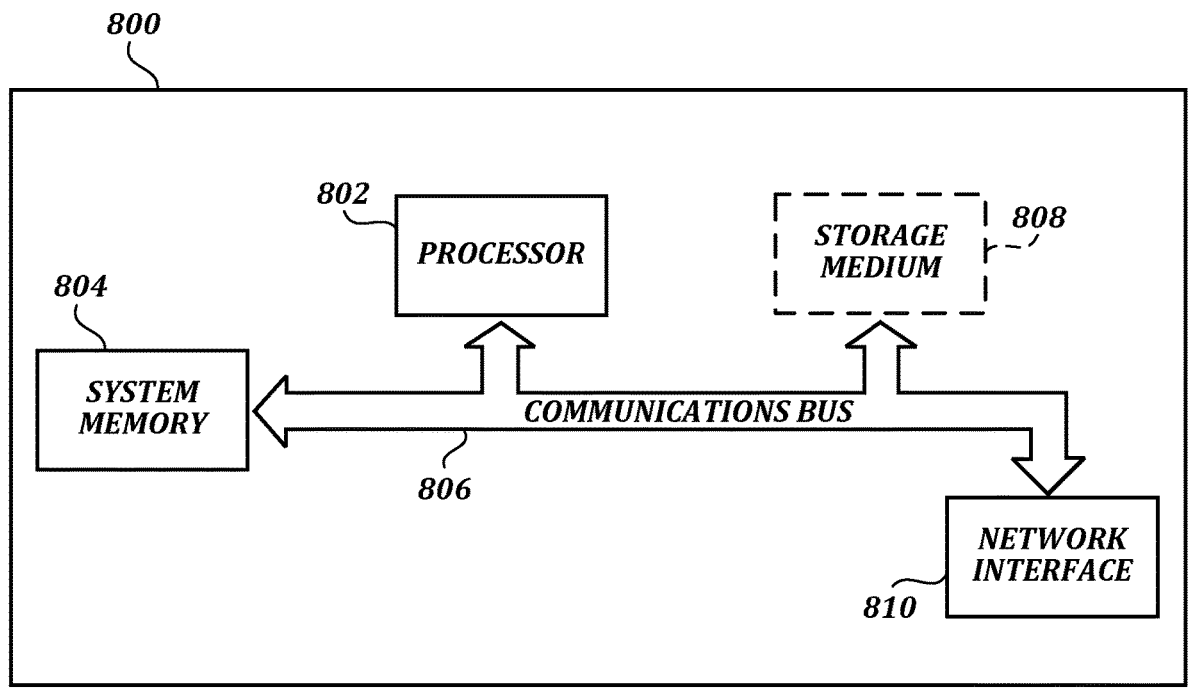
FIG. 6 is a block diagram that illustrates aspects of an example computing device, in accordance with various embodiments.

FIG. 6 is a block diagram that illustrates aspects of an example computing device 600, in accordance with various embodiments. While multiple different types of computing devices are described in reference to the various embodiments, the example computing device 600 describes various elements that are common to many different types of computing devices. While FIG. 6 is described with reference to a computing device that is implemented as a device on a network, the description below is applicable to servers, personal computers, mobile phones, smart phones, tablet computers, embedded computing devices, and other devices that can be used to implement portions of embodiments of the present disclosure. Moreover, those of ordinary skill in the art and others will recognize that the computing device 600 can be any one of any number of currently available or yet to be developed devices. In this way, the description of FIG. 6 can be applied to constituent components of the example system 100 of FIG. 1, including but not limited to the hair contouring device 104, the client computing device(s) 130, and/or the server(s) 160.

In its most basic configuration, the example computing device 600 includes at least one processor 602 and a system memory 604 connected by a communication bus 606. Depending on the exact configuration and type of device, the system memory 604 can be volatile or nonvolatile memory, such as read only memory ("ROM"), random access memory ("RAM"), EEPROM, flash memory, or similar memory technology. Those of ordinary skill in the art and others will recognize that system memory 604 typically stores data and/or program modules that are immediately accessible to and/or currently being operated on by the processor 602. In this regard, the processor 602 can serve as a computational center of the computing device 600 by supporting the execution of instructions.

As further illustrated in FIG. 6, the computing device 600 can include a network interface 610 comprising one or more components for communicating with other devices over a network. Embodiments of the present disclosure can access basic services that utilize the network interface 610 to perform communications using common network protocols. The network interface 610 can also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 610 illustrated in FIG. 6 can represent one or more wireless interfaces or physical communication interfaces described and illustrated above with respect to particular components of the system 100 of FIG. 1.

In the exemplary embodiment depicted in FIG. 6, the computing device 600 also includes a storage medium 608. However, services can be accessed using a computing device that does not include means for persisting data to a local storage medium. Therefore, the storage medium 608 depicted in FIG. 6 is represented with a dashed line to indicate that the storage medium 608 is optional. In any event, the storage medium 608 can be volatile or nonvolatile, removable or nonremovable, implemented using any technology capable of storing information including, but not limited to, a hard disk drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 604 and storage medium 608 depicted in FIG. 6 are merely examples of computer-readable media.

Suitable implementations of computing devices that include a processor 602, system memory 604, communication bus 606, storage medium 608, and network interface 610 are known and commercially available. For ease of illustration and because it is not important for an understanding of the claimed subject matter, FIG. 6 does not show some of the typical components of many computing devices. In this regard, the example computing device 600 can include input devices, such as a keyboard, keypad, mouse, microphone, touch input device, touch screen, and/or the like. Such input devices can be coupled to the example computing device 600 by wired or wireless connections including RF, infrared, serial, parallel, Bluetooth, Bluetooth low energy, USB, or other suitable connections protocols using wireless or physical connections. Similarly, the example computing device 600 can also include output devices such as a display, speakers, printer, etc. Since these devices are well known in the art, they are not illustrated or described further herein.

While illustrative embodiments have been illustrated and described, it will be appreciated that various changes can be made therein without departing from the spirit and scope of the invention. It is to be understood that the methods and systems described herein are not limited to specific methods, specific components, or to particular implementations. It is also to be understood that the terminology used herein is for the purpose of describing embodiments only and is not intended to be limiting.

As used in the specification and the appended claims, the singular forms "a," "an" and "the" include plural referents unless the context clearly dictates otherwise. Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance can or can not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

The embodiments of the invention in which an exclusive property or privilege is claimed are defined as follows:

1. A hair contouring device, comprising:
   a contouring source, configured to generate contouring electromagnetic radiation within a first energy range to induce a conformation change of a hydrogel formulation; and
   a fixing source, configured to generate curing electromagnetic radiation within a second energy range to induce a photo-curing transition of the hydrogel formulation;
   an input component;
   control circuitry, electrically coupled with the contouring source, the fixing source, and the input component, the control circuitry being configured to receive an input from the input component and to control the contouring source or the fixing source in accordance with the input;
   a radiation sensor, electronically coupled with the control circuitry; and
   one or more non-transitory memory devices, electronically coupled with the control circuitry and storing computer-readable instructions that, when executed by one or more processors of the control circuitry, cause the control circuitry to perform operations comprising:
   generating a mapping of a biological surface using the radiation sensor, the biological surface comprising hair and the hydrogel formulation, the mapping describing a volume of the hair relative to the biological surface;
   generating a projection of a hair contouring design onto the mapping, wherein the hair contouring design defines a contouring treatment to be applied to the volume of the hair; and
   determining an exposure profile and an exposure duration using the projection
   exposing the volume of the hair to the contouring electromagnetic radiation using the contouring source in accordance with the exposure profile and the exposure duration; and
   exposing the volume of the hair to the curing electromagnetic radiation using the fixing source.

2. The hair contouring device of claim 1, wherein the conformation change of the hydrogel formulation comprises a volumetric expansion or contraction of the hydrogel formulation.

3. The hair contouring device of claim 1, wherein the photo-curing transition of the hydrogel formulation comprises a crosslinking of the hydrogel formulation.

4. The hair contouring device of claim 1, wherein:
   the input comprises a contouring control or a fixing control;
   the control circuitry is configured to activate the contouring source in response to receiving the contouring control; and
   the control circuitry is configured to activate the curing source in response to receiving the fixing control.

5. The hair contouring device of claim 1, wherein the instructions, when executed by the one or more processors, further cause the control circuitry to perform operations comprising:
   receiving the hair contouring design via the input component, wherein the input component comprises communication circuitry configured to pair with a client computing device and to receive the input from the client computing device.

6. The hair contouring device of claim 1, wherein the hydrogel formulation comprises photo-responsive filaments, and wherein the photo-responsive filaments exhibit anisotropic deformation in response to exposure to the contouring electromagnetic radiation.

7. The hair contouring device of claim 1, wherein the first energy range corresponds to near-ultraviolet wavelengths from about 300 nm to about 400 nm.

8. The hair contouring device of claim 1, wherein the first energy range corresponds to near-infrared wavelengths from about 750 nm to about 1400 nm.

9. The hair contouring device of claim 8, wherein the hydrogel formulation comprises upconverting nanoparticles, wherein the upconverting nanoparticles emit ultraviolet photons when exposed to the contouring electromagnetic radiation.

10. The hair contouring device of claim 1, wherein the first energy range corresponds to visible wavelengths from about 400 nm to about 750 nm.

11. The hair contouring device of claim 1, wherein the hydrogel formulation comprises a photo-initiator dispersed in poly(ethylene glycol) diacrylate.

12. The hair contouring device of claim 1, wherein the hydrogel formulation comprises an absorber material dispersed in a hydrogel comprising poly(N-isopropylacrylamide) (pNIPAm) copolymerized with spiropyrane.

13. The hair contouring device of claim 12, wherein the absorber material comprises chromium oxide or iron oxide particles.

14. The hair contouring device of claim 1, wherein the second energy range corresponds to near-ultraviolet wavelengths, visible wavelengths, or near-infrared wavelengths, being non-overlapping with the first energy range.

15. A method of contouring hair using a hydrogel formulation and a device of claim 1, the method comprising:
  applying the hydrogel formulation to a volume of hair;
  exposing the volume of hair to contouring electromagnetic radiation within a first energy range to induce a conformation change of the hydrogel formulation, the conformation change comprising a volumetric expansion or contraction of the hydrogel formulation; and
  exposing the volume of hair to curing electromagnetic radiation within a second energy range to induce a photo-curing transition of the hydrogel formulation, the photo-curing transition comprising a crosslinking of the hydrogel formulation;
  wherein the contouring electromagnetic radiation and the curing electromagnetic radiation are generated by a hair contouring device comprising a contouring source of the contouring electromagnetic radiation, a fixing source of the curing electromagnetic radiation, an input component, and control circuitry, the control circuitry being electrically coupled with the contouring source, the radiation sensor, the fixing source, and the input component.

16. The method of contouring hair of claim 15, further comprising:
  generating a mapping of the volume of hair using a radiation sensor, the radiation sensor being electronically coupled with the control circuitry;
  generating a projection of a hair contouring design onto the mapping, wherein the hair contouring design defines a contouring treatment to be applied to the volume of hair; and
  determining an exposure profile and an exposure duration using the projection,
  wherein exposing the volume of hair to the contouring electromagnetic radiation comprises controlling the contouring source in accordance with the exposure profile and the exposure duration.

17. The method of contouring hair of claim 16, further comprising:
  receiving the hair contouring design via communication circuitry configured to pair with a client computing device and to receive the input from the client computing device.

18. The method of contouring hair of claim 15, further comprising:
  receiving an input from the input component, the input comprising a contouring control or a fixing control;
  activating the contouring source in response to receiving the contouring control; and
  activating the fixing source in response to receiving the fixing control.

19. The method of contouring hair of claim 15, wherein the hydrogel formulation comprises photo-responsive filaments, and wherein the photo-responsive filaments exhibit anisotropic deformation in response to exposure to the contouring electromagnetic radiation.

* * * * *